United States Patent [19]

Oakes et al.

[11] Patent Number: 4,794,362

[45] Date of Patent: Dec. 27, 1988

[54] ALTERNATING CURRENT POWER CIRCUIT AND FUSE THEREFOR

[75] Inventors: Martin C. Oakes; David W. Klaus, both of Leeds, England

[73] Assignee: Y.S. Securities Limited, West Yorkshire, England

[21] Appl. No.: 142,465

[22] Filed: Jan. 11, 1988

[30] Foreign Application Priority Data

Jan. 10, 1987 [GB] United Kingdom ................. 8700530

[51] Int. Cl.$^{4}$ ............................................. A01H 85/04

[52] U.S. Cl. ............................... 337/158; 200/144 A; 337/32; 337/273

[58] Field of Search .................... 337/158, 163, 17, 32, 337/199, 273, 145; 200/144, 147

[56] References Cited

U.S. PATENT DOCUMENTS 4,692,733 9/1987 Oakes ................................ 337/158

*Primary Examiner*—H. Broome

*Attorney, Agent, or Firm*—Henry Sternberg; Bert J. Lewen

[57] ABSTRACT

A fuse for an alternating current power circuit. The fuse comprises an input terminal (4), a first contact (5) electrically connected to the input terminal, an output terminal (9) and a second contact (8) electrically connected to the output terminal. A fusible element (11) electrically connects the first and second contacts and completes a normal electrical path between the input and output terminals. An arcing contact (6) is positioned in relation to the first contact (5) so as to form a potential arc path between the first contact and the arcing contact, along which path an arc will become established after the fusible element breaks in response to fault current. The arcing contact (6) is electrically connected to a third terminal (41) and is electrically isolated from the output terminal (9).

The fuse can be used in a single phase circuit to reduce let-through energy to a load under fault conditions, or in each phase of a multi-phase circuit to break the supply to all phases in response to a fault on any one phase.

10 Claims, 5 Drawing Sheets

ALTERNATING CURRENT POWER CIRCUIT AND FUSE THEREFOR

This invention relates to an alternating current power circuit, and to a fuse therefor, and is concerned with both single-phase and multi-phase circuits.

GB-A No. 2179508 describes a fuse for an alternating current power circuit that comprises an input and an output terminal, first and second contacts electrically connected respectively to the input and output terminals and a fusible element electrically connecting the first and second contacts to complete a normal electrical path between the terminals. The contacts and the fusible element are enclosed in a sealed chamber filled with an electo-negative halogenated medium, such as sulphur hexafluoride. In the presence of fault current the fusible element melts, causing an arc to be struck, and the arc becomes established between the first contact, which forms a first electrode having a substantially circular periphery, and an arcing electrode having a conductive surface internally of the chamber and radially surrounding the first electrode. A coil is connected between the arcing contact and the second terminal, and is positioned so that when energised the magnetic field induced by the fault current flowing in the coil will cause the arc to rotate around the first electrode and to become extinguished in the electronegative medium.

The arc will only be extinguished at or around current zero, and the fuse does not significantly force a current zero in the manner of conventional current-limiting fuses. Accordingly, the full energy of the first current loop is allowed to pass into the fault zone. For urban network use, this is not a significant disadvantage, especially when comparisons are made with the let-through energies of many types of circuit breaker now in use in such systems. However, in some industrial uses, e.g. for electric motors, high let-through energies are disadvantageous, in that it is common to connect the motor to its supply by cable that is capable of withstanding normal current and low value fault current, but can not withstand full system fault current without suffering thermal or electodynamic damage. Accordingly, it would be advantageous if the let-through energy of the fuse could be reduced. Similarly, it would be advantageous to reduce the let-through energy of other types of fuse, circuit breaker or switching device, which rely for their operation upon the drawing of an arc to an arcing electrode. Hereinafter all such devices will be referred toggenerically as "fuses". A further example of such a fuse is shown in DE-A No. 548914.

With multi-phase supply networks the practice in the United States is generally to interrupt only one phase of a supply if a fault occurs on that phase, but to maintain the other phases. In the United Kingdom and elsewhere it is more common to interrupt all phases in response to a fault condition occurring on any one phase. The fuse as aforesaid can only protect a single phase, and the present invention thus also concerns itself with a fuse arrangement which will enable substantially simultaneous interruption of all phases of a multi-phase circuit in response to fault current on one phase only.

According to a first aspect of the invention a fuse for an alternating current power circuit comprises an input terminal, a first contact electrically connected to the input terminal, an output terminal, a second contact electrically connected to the output terminal, a fusible element electrically connecting the first and second contacts and completing a normal electrical path between the input and output terminals, and an arcing contact positioned in relation to the first contact so as to form a potential arc path between the first contact and the arcing contact, along which path an arc will become established after the fusible element breaks in response to fault current, characterised in that the arcing contact is electrically connected to a third terminal and is electrically isolated from the output terminal.

In the construction described in GB-A No. 2179508 the arcing contact is elecrically connected to the output terminal; the fuse of the present invention differs in that the arcing contact is isolated from the output terminal and connected to a third terminal. Advantage can be gained by this in both single phase and multi-phase circuits, as will hereinafter be explained.

According to a second aspect of the invention a single phase alternating power circuit comprises a fuse as aforesaid, a supply conductor electrically connected to the input terminal of the fuse, a load conductor electrically connected to the output terminal of the fuse, and a return conductor electrically connected to the third terminal of the fuse.

As the third terminal is electrically connected to a return conductor it will readily be seen that, after the fusible element has been broken under fault conditions, the fault current forming the arc is diverted from the load conductor and connected load. The let-through energy from the fuse is thus significantly reduced. Preferably the return conductor is, or is connected to, earth. Further advantage may be obtained if the return conductor is connected to the third terminal of the fuse either by way of an impedance or by way of a current-limiting fuse, as will be further explained.

According to a third aspect of the invention a three phase alternating current power circuit comprises first, second and third fuses, each as aforesaid, a first supply conductor electrically connected to the input terminal of the first fuse, a first load conductor electrically connected to the output terminal of the first fuse, a second supply conductor electrically connected to the input terminal of the second fuse, a second load conductor electrically connected to the output terminal of the second fuse, a third supply conductor electrically connected to the input terminal of the third fuse, and a third load conductor electrically connected to the output terminal of the third fuse, in which the third terminal of the first fuse is electrically connected to the output terminal of the second fuse, the third terminal of the second fuse is electrically connected to the output terminal of the third fuse, and the third terminal of the third fuse is electrically connected to the output terminal of the first fuse.

When fault current is experienced on one phase, the fusible element of the fuse in that phase breaks, and the fault current flowing in the arc is passed to the output terminal of the fuse of a second phase. This short circuit is perceived as a fault by the fuse of the second phase, so that the fusible element of the fuse in the second phase breaks, and the fault current in the resultant arc is passed to the output terminal of the third phase to form a further short circuit. Thus, all three phases are interrupted in response to fault current in any one phase.

In multi-phase circuits having other than three phases a fuse according to the invention will be incorporated in each phase, and the third terminal of each fuse will be connected to the output terminal of the fuse of a different phase in such a way that each output terminal is connected to the third terminal of a different fuse.

If the roots of a high current arc are allowed to remain stationary on the contacts between which the arc is drawn for any length of time then there will be considerable damage to those contacts, and indeed there may be catastrophic destruction of the whole fuse. Accordingly, it is preferred to incorporate in the fuse arc moving means operative when an arc is established between the first contact and the arcing contact to move one arc root on the surface of the first contact and to move the other arc root on the surface of the arcing contact. Preferably the arc moving means is a coil electrically connected between the arcing contact and the third terminal. As described in GB-A No. 2179508 such a coil, when so energised, will cause rotation of the arc around the first contact. The current in the coil will, of course, flow to a return conductor or to a connected phase, rather than to the fault location. In alternative arrangements, the coil may be replaced by a permanent magnet or other arrangement capable of creating an electromagnetic field.

The invention will be better understood from the following description of specific embodiments thereof, given in conjunction with the accompanying drawings in which.

Figure 1:
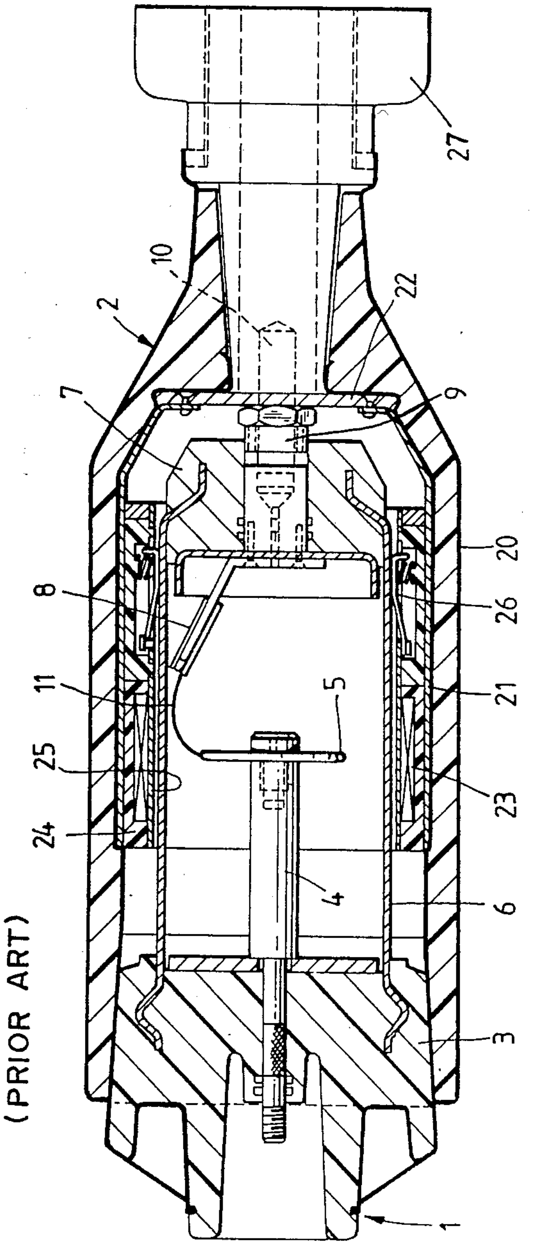
FIG.1. (PRIOR ART)
FIG. 1 is a longitudinal cross-section through a typical fuse as described in GB-A No. 2179508.

The fuse shown in FIG. 1 is formed in two parts shown generally as 1 and 2 respectively, the first part fitting within the second part. The first part comprises a carrier 3 cast or moulded from any suitable insulating material and having an input terminal 4 extending through the carrier and being cast or moulded in situ therein, or secured in any other suitable way, such as by an adhesive. At the end of the terminal there is a first contact 5 having a circular periphery forming a first arcing electrode. A copper cylinder 6 extends from the carrier 3 to a mounting block 7 also of insulating material. The mounting block support a second contact 8 electrically connected to an output terminal 9 having a threaded spigot 10 extending therefrom. The first and second contacts 5 and 8 are electrically connected by a fusible element 11. The inner surface of the copper cylinder 6 forms an arcing contact lying internally of the chamber and radially surrounding and radially spaced from the first contact 5. The cylinder is filled with an electronegative medium such as sulphur hexafluoride.

The second part 2 of the fuse comprises an insulating housing 20 having a sleeve 21 of conductive material bonded to part of the inner surface thereof and connected to a conductive disc 22 that is in electrical contact with the output terminal 10. A coil 23 is cast or moulded into a block 24 of insulating material, and that block is bonded to the sleeve 21. One end of the coil winding is electrically connected to the sleeve 21, and the other end is electrically connected to a ring 25 that constitutes a coil former and a shorted innermost turn of the coil. The ring 25 is electrically connected to fingers 26 that engage the copper cylinder 6 when the two fuse parts are assembled as shown in FIG. 1.

In normal operation, a supply conductor is connected to the input terminal 4, and a load conductor is connected to the output terminal 9. The load conductor may be embodied in a bushing 27 forming part of, for example, switchgear or a transformer, and may be secured onto the spigot 10. A normal current path is established through the fuse between the terminals 4 and 10 by way of the contacts 5 and 8 and the connecting fusible element 11. In the event of a fault causing an overcurrent, the element 11 will melt and an arc will be struck from the contact 5 towards the contact 8. However, due to magnetic loop forces the arc will commutate from the contact 8 onto the inner surface of the copper cylinder 6, so causing the arcing current to flow through the coil 23 and to the output terminal 9. The magnetic field induced in the coil will cause rotation of the arc, which will be extinguished in the electro-negative medium at or near to a current zero.

Further detail of the fuse described above and its operation is given in GB-A No. 2179508, which also describes other types of fuse, all of which may be modified for use in the present invention.

Figure 2:
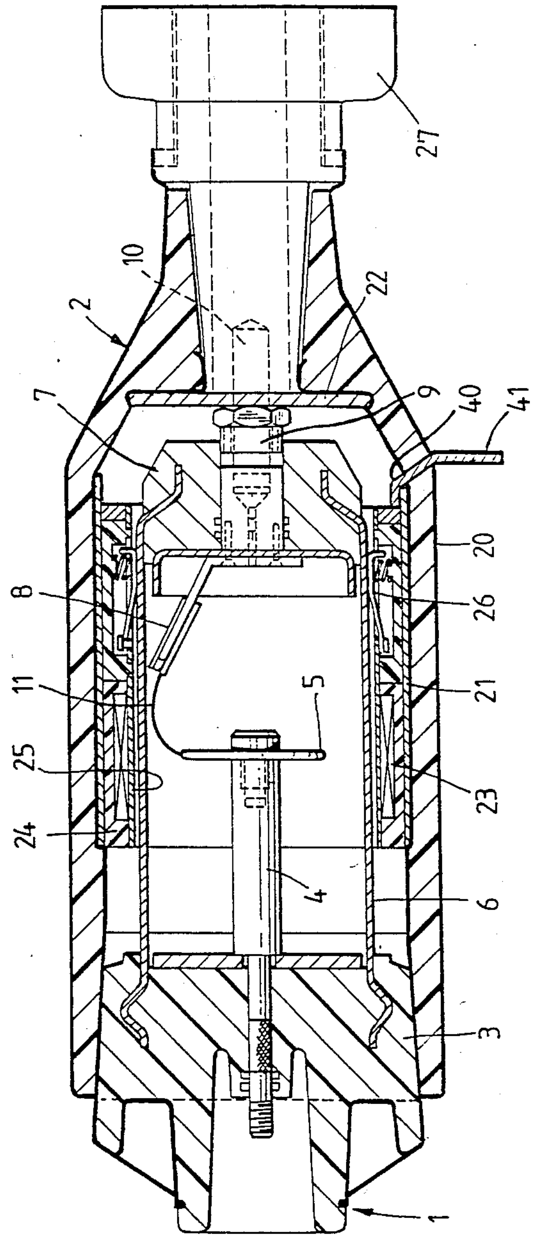
FIG. 2 shows a fuse similar to that of FIG. 1, but modified so as to be in accordance with the invention.

FIG. 2 shows the fuse of FIG. 1 modified according to the invention. The modification comprises removing the electrical connection between the sleeve 21 and the ring 22, so that the sleeve is electrically isolated from the output condcctor 10. In place of this connection, a conductor 40 is moulded in situ in the housing 10 to make electrical contact with the sleeve 21 and to provide a third terminal 41 lying outside the housing.

Figure 3:
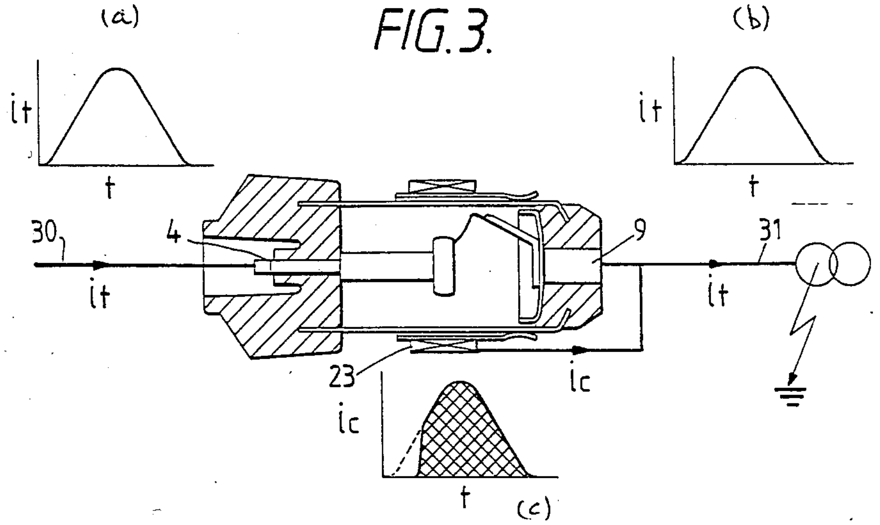
FIG. 3 shows schematically the fuse of FIG. 1 in a single-phase alternating current power circuit, and shows also current diagrams within the circuit.

FIG. 3 illustrates diagramatically the fuse of FIG. 1 with a single phase alternating current source connected to input terminal 4 by a supply conductor 30, and the output terminal 9 connected by a load conductor 31 to an electrical load. If a fault should occur then, as already described, the fusible element melts and arc current flows through the coil. The graphs of current against time show: (a) system prospective current, (b) current flowing in the coil and (c) let-through current passed to the load. The current is only extinguished at current zero, and accordingly the let-through current is substantially the same as the system prospective current, so that the let-through energy is high.

Figure 4:
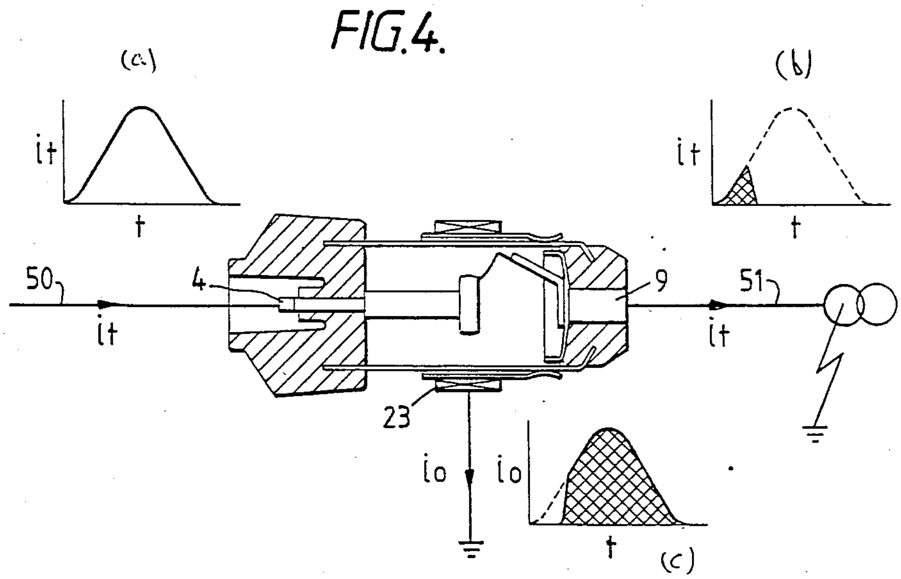
FIGS. 4 to 6 are similar to FIG. 3, but represent different embodiments of single phase alternating current power circuits according to the invention utilising the fuse of FIG. 2.

FIG. 4 shows the fuse of FIG. 2 connected in a single phase alternating current power circuit. A supply conductor 50 is connected to input terminal 4, a load conductor 51 is connected to output terminal 9, and the third terminal 41 is connected directly to earth. Accordingly, if a fault condition occurs, the fault current will melt the fusible element and the resultant arc will commutate onto the inner surface of the cylinder 6 as already described. The arc current will then flow through the coil 23 to earth and the electromagnetic field induced in the coil will cause the arc to rotate and to become extinguished at current zero. The current/time curves on (a) the supply conductor 50, (b) the load conductor 51 and (c) through the coil are shown in the Figure. It will be noted that the system prospective current and coil current are similar to those shown in FIG. 3. However, as the fault current flows to earth rather than to the fault region the let-through current starts to fall to zero as soon as the arc has commutated onto the cylinder. Accordingly, the let-through energy to the fault is very much lower than in the FIG. 3 embodiment.

Figure 5:
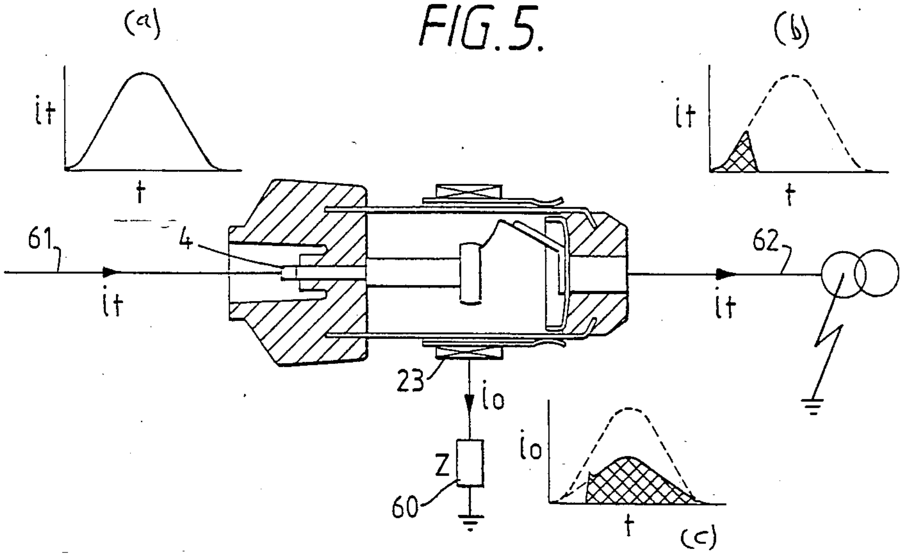

In the embodiment shown in FIG. 5 the third terminal 41 is connected to earth through an impedance 60. Operation under fault conditions is analogous to that already described and current/time curves are shown on (a) the supply conductor 61, (b) the load conductor 62 and (c) in the coil. It will be seen that the effect of the impedance is to reduce the current flowing in the coil as will be seen from the coil current/time curve. Accordingly, a fuse designed to deal with a given fault current may be made less robust in construction than would otherwise be the case, alternatively a fuse of given construction is able to handle a higher fault current by incorporating an impedance between the coil and earth. It will be noted that the let-through current continues to be low.

Figure 6:
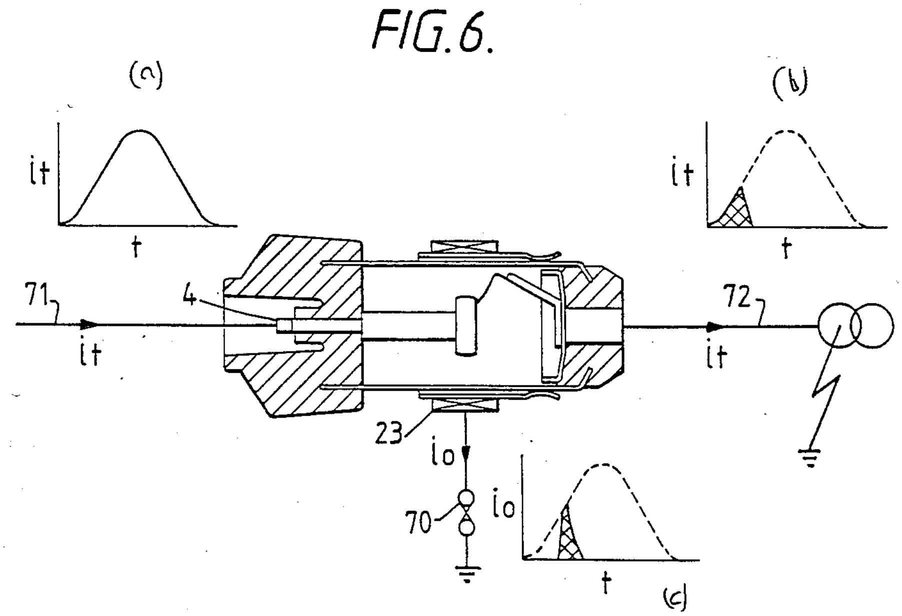

In the embodiment shown in FIG. 6 the third terminal 41 of the fuse is connected to earth through a currentlimiting fuse 70, which may be of any suitable construction, for example a conventional cartridge fuse capable of handling currents in the range of 2 to 20 amps. Again, current/time curves are shown for (a) the supply conductor 71, (b) the load conductor 72 and (c) the coil. In this embodiment, hhe fault current will flow through the coil and the current path will be broken very quickly as the fuse 70 forces the current to zero prior to the natural current zero of the supply. The arc is thus extinguished. It will again be seen that the let-through current is low, and that the current flowing in the coil is still further reduced from that obtained with the FIG. 5 embodiment. As a consequence, very much lighter fuse constructions can be used and/or very much higher fault currents can be handled for a given coil construction.

In each of FIGS. 4 to 6 a simple earth connection is shown. It will be appreciated, however, that the return conductor of the uupply will commonly also be connected to earth, and the connection may then be to the return conductor rather than direct to earth. In other embodiments the return conductor may not be earthed, and the earth connection can then be replaced by one to the return conductor.

Figure 7:
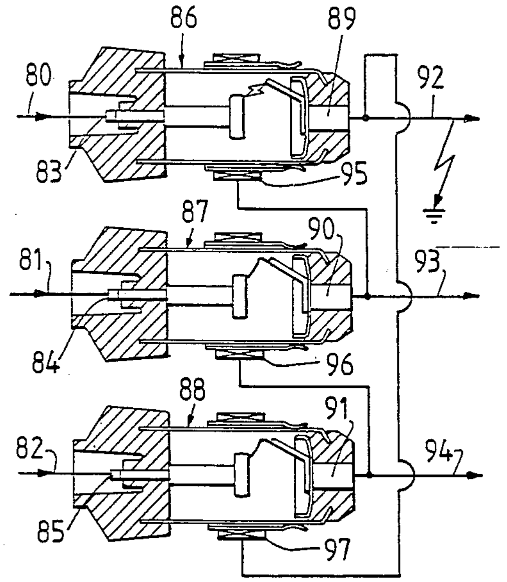
FIGS. 7 to 9 show schematically a three phase alternating current power circuit according to the invention, utilising fuses as shown in FIG. 2, at different stages of operation.
Figure 8:
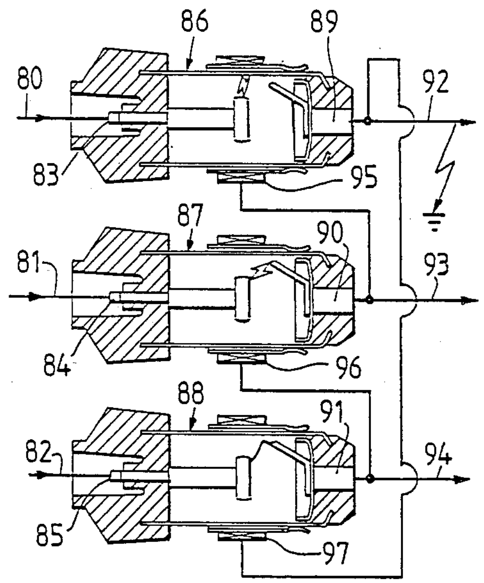
Figure 9:
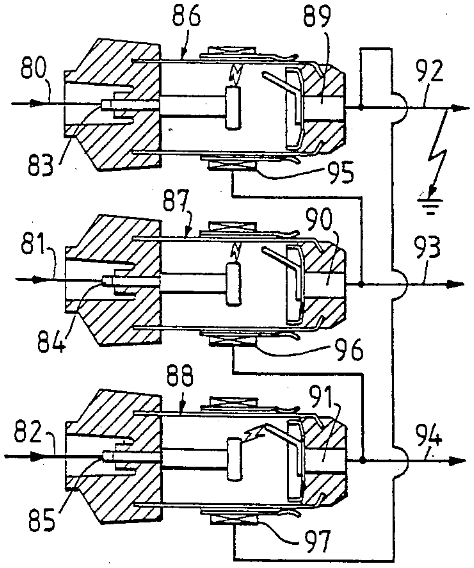

FIGS. 7 to 9 show an arrangement for protecting a three-phase current supply having three supply conductors 80 to 82 connected to input terminals 83 to 85 of respective fuses 86 to 88, the respective output terminals 89 to 91 of which are connected to load conductors 92 to 94. The coils 95 to 97 of the three phases are each connected by way of the third terminal of the respective fuse to the output terminal of an adjacent phase as shown in the Figure. Assume that a fault occurs on that phase of the equipment connected to supply conductor 92. The fusible element of fuse 86 will melt, causing an arc (FIG. 7), which will commutate onto the inner surface of the cylinder. Arc current will flow through the coil 95 to the output terminal 90 and load conductor 93, and the magnetic field induced by the coil 95 will rotate the arc in fuse 86, the arc being extinguished at a current zero on that phase. However, the current flowing through the coil 95 to load conductor 93 will be detected a fault current by the fuse 87, so causing the fusible element of that fuse to melt, and arcing (FIG. 8) to occur to energise coil 96 and pass the fault current to output terminal 91 of fuse 88, and to load conductor 94. The arc of fuse 87 will be rotated and will be extinguished at current zero. The referred current in the third phase will again be detected as fault current, causing arcing in fuse 88 as shown in FIG. 9. Extinction of the arc in fuse 87 will break the current path through both fuses 87 and 88 so that the arc in the latter fuse will be extinguished substantially simultaneously with that in fuse 87. It will be appreciated that the interconnections shown will thus automatically lead to interruption of all three phases in response to fault current on any one phase.

Figure 10:
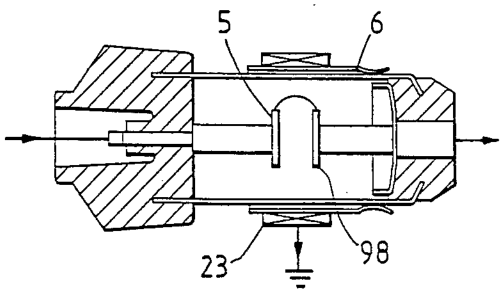
FIG. 10 is a schematic longitudinal cross-section of a second embodiment of fuse according to the invention.

The fuses described thus far are unidirectional, in that they will only operate properly if connected so that the supply is connected to input terminal 4 and the load to output terminal 9. If the fuse were wrongly connected, then the resultant arc between the contact 8 and the inner surface of cylinder 6 would not be rotated. FIG. 10 shows a modified form of fuse which avoids this disadvantage and will give circuit protection if either of the input and output terminals is connected to the supply, and the other connected to the load. In this embodiment, the contact 8 is replaced by a circular contact 98, of the same diameter as contact 5, and both contacts 5 and 98 lie axially within the confines of the coil 23. A fault on one side of the fuse will cauee arcing between contact 98 and the cylinder 6, a fault on the other side will cause arcing between contact 5 and cylinder 6. In either case, arc current will flow in the coil, and as the arc lies within the magnetic field induced thereby it will be rotated and extinguished.

It will be understood that other types of fuse relying on arc extinction to break a current path may be used, in each of the FIGS. 2 to 6 embodiments, so long as the arcing contact is electrically isolated from the output terminal and is electrically connected to a third terminal, and that similar advantages may result therefrom. It will also be understood that the third terminal may be of any suitable form allowing connection to, or already forming an integral connection with, a return conductor or other phase of a supply.

We claim:

1. A fuse for an alternating current power circuit, the fuse comprising an input terminal, a first contact electrically connected to the input terminal, an output terminal, a second contact electrically connected to the output terminal, a fusible element electrically connecting the first and second contacts and completing a normal electrical path between the input and output terminals, and an arcing contact positioned in relation to the first contact so as to form a potential arc path between the first contact and the arcing contact, along which path an arc will become established after the fusible element breaks in response to fault current, characterised in that the arcing contact is electrically connected to a third terminal and is electrically isolated from the output terminal.

2. A fuse according to claim 1 and including arc moving means operative when an arc is established between the first contact and the arcing contact to move one arc root on the surface of the first contact and to move the other arc root on the surface of the arcing contact.

3. A fuse according to claim 2 in which the arc moving means comprises a coil electrically connected between the arcing contact and the third terminal.

4. A fuse according to claim 3 in which the fuse comprises a sealed chamber filled with an electronegative halogenated medium, the first contact is mounted within the chamber and has a substantially circular periphery forming a first arcing electrode, and the arcing contact comprises a second arcing electrode having a conductive surface internally of the chamber, the conductive surface surrounding and being radially spaced from the first arcing electrode.

5. A fuse according to claim 4 in which the coil radially surrounds the chamber, and the radial mid-planes of the coil and of the circumference of the first electrode are substantially coincident.

6. A single phase alternating current power circuit comprising a fuse according to claim 1, a supply conductor electrically connected to the input terminal of the fuse, a load conductor electrically connected to the output terminal of the fuse, and a return conductor electrically connected to the third terminal of the fuse.

7. A circuit acoording to claim 6 in which the return conductor is, or is connected to, earth.

8. A circuit according to claim 6 in which the return conductor is electrically connected to the third terminal of the fuse by way of an impedance.

9. A circuit according to claim 6 in which the return conductor is electrically connected to the third terminal of the fuse by way of a current limiting fuse.

10. A three phase alternating current power circuit comprising first, second and third fuses each according to claim 1, a first supply conductor electrically connected to the input terminal of the first fuse, a first load conductor electrically connected to the output terminal of the first fuse, a second supply conductor electrically connected to the input terminal of the second fuse, a second load conductor electrically connected to the output terminal of the second fuse, a third supply conductor electrically connected to the input terminal of the third fuse, and a third load conductor electrically connected to the output terminal of the third fuse, in which the third terminal of the first fuse is electrically connected to the output terminal of the second fuse, the third terminal of the second fuse is electrically connected oo the output terminal of the third fuse, and the third terminal of the third fuse is electrically connected to the output terminal of the first fuse.

* * * * *